United States Patent
Läuger et al.

(10) Patent No.: US 9,766,172 B2
(45) Date of Patent: Sep. 19, 2017

(54) DOUBLE-MOTOR RHEOMETER WITH EXTENSION ASSEMBLY

(71) Applicant: Anton Paar GmbH, Graz (AT)

(72) Inventors: Jörg Läuger, Stuttgart (DE); Michael Krenn, Zettling (AT); Gabriele Köpping, Gratkorn (AT)

(73) Assignee: Anton Paar GmbH, Graz (AT)

( * ) Notice: Subject to any disclaimer, the term of this patent is extended or adjusted under 35 U.S.C. 154(b) by 579 days.

(21) Appl. No.: 14/254,664

(22) Filed: Apr. 16, 2014

(65) Prior Publication Data

US 2014/0311224 A1    Oct. 23, 2014

(30) Foreign Application Priority Data

Apr. 20, 2013  (DE) .................. 10 2013 207 184

(51) Int. Cl.
*G01N 11/14*    (2006.01)
*G01N 11/00*    (2006.01)

(52) U.S. Cl.
CPC ............. *G01N 11/14* (2013.01); *G01N 11/00* (2013.01); *G01N 11/142* (2013.01)

(58) Field of Classification Search
CPC ........ G01N 11/14; G01N 11/00; G01N 11/10; G01N 11/142; G01N 11/02
USPC ............ 73/54.28, 54.01, 54.02, 54.35, 54.39
See application file for complete search history.

(56) References Cited

U.S. PATENT DOCUMENTS

| | | | | |
|---|---|---|---|---|
| 3,803,903 A | * | 4/1974 | Lin | G01N 11/14 73/54.28 |
| 4,559,812 A | * | 12/1985 | Kitchen | G01N 11/14 374/47 |
| 5,277,058 A | * | 1/1994 | Kalyon | G01N 11/04 73/54.11 |
| 6,578,413 B2 | | 6/2003 | Sentmanat | |
| 6,691,569 B1 | | 2/2004 | Sentmanat | |
| 2001/0049972 A1 | | 12/2001 | Sentmanat | |

(Continued)

FOREIGN PATENT DOCUMENTS

| | | |
|---|---|---|
| DE | 202 17 272 U1 | 2/2003 |
| DE | 10 2008 010 967 A1 | 9/2009 |
| GB | 2 429 299 A | 2/2007 |

*Primary Examiner* — Hezron E Williams
*Assistant Examiner* — Marrit Eyassu
(74) *Attorney, Agent, or Firm* — Robert A. Blaha; Smith Tempel Blaha LLC

(57) ABSTRACT

An extension assembly is connected or connectable, in terms of driving, to a double-motor rheometer. The double-motor rheometer includes first and second measuring motors controllable independently of each other, and provided for determining a torsional moment generated by the corresponding measuring motor. The extension assembly includes first and second sample holding parts for holding a first sample portion and a second sample portion of the sample. The first sample holding part is driveable by the first measuring motor in a rotational movement about a first axis, and the second sample holding part is driveable by the second measuring motor in a rotational movement about a second axis. The first axis is arranged so as to be parallel to and spaced apart from the second axis. The sample held in the first sample portion and in the second sample portion extends between the respective sample holding parts.

16 Claims, 4 Drawing Sheets

(56) References Cited

U.S. PATENT DOCUMENTS

| | | | |
|---|---|---|---|
| 2004/0020287 A1* | 2/2004 | Sentmanat | G01N 3/08 |
| | | | 73/261 |
| 2007/0292004 A1 | 12/2007 | Peters | |
| 2008/0022758 A1* | 1/2008 | Cottais | G01N 11/142 |
| | | | 73/54.32 |
| 2011/0100098 A1* | 5/2011 | Lauger | G01N 11/142 |
| | | | 73/54.28 |
| 2012/0234081 A1 | 9/2012 | Maia et al. | |
| 2014/0137638 A1* | 5/2014 | Liberzon | G01N 11/14 |
| | | | 73/54.28 |

* cited by examiner

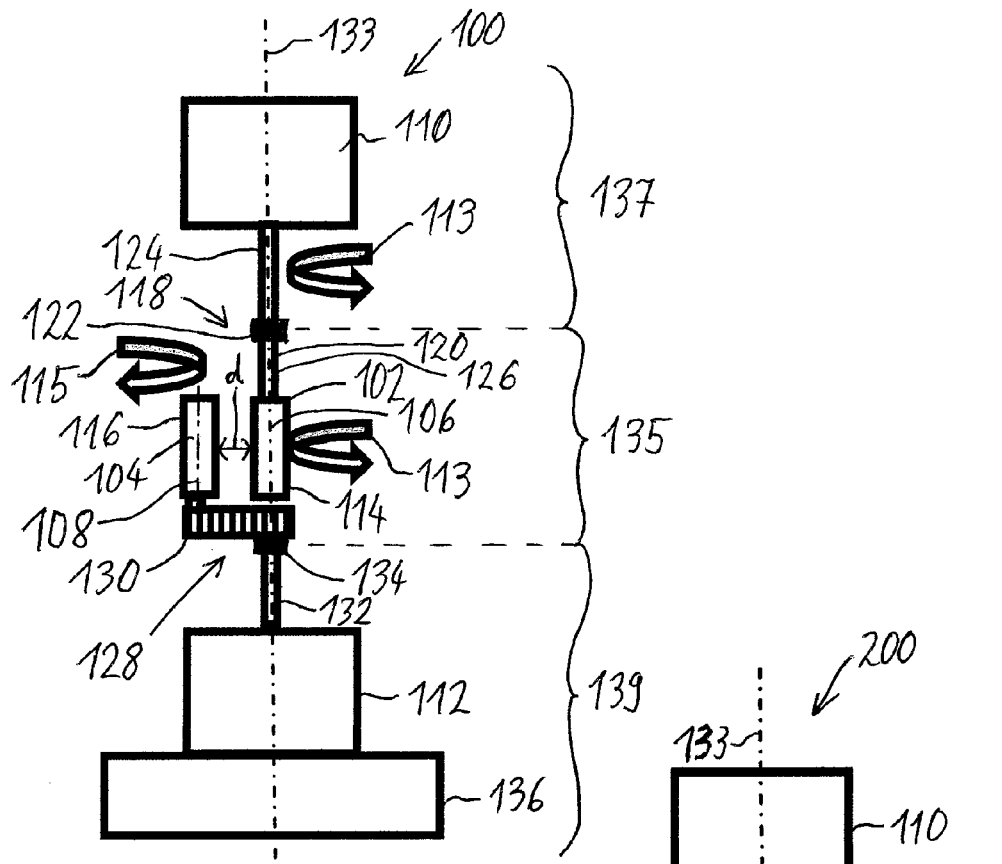
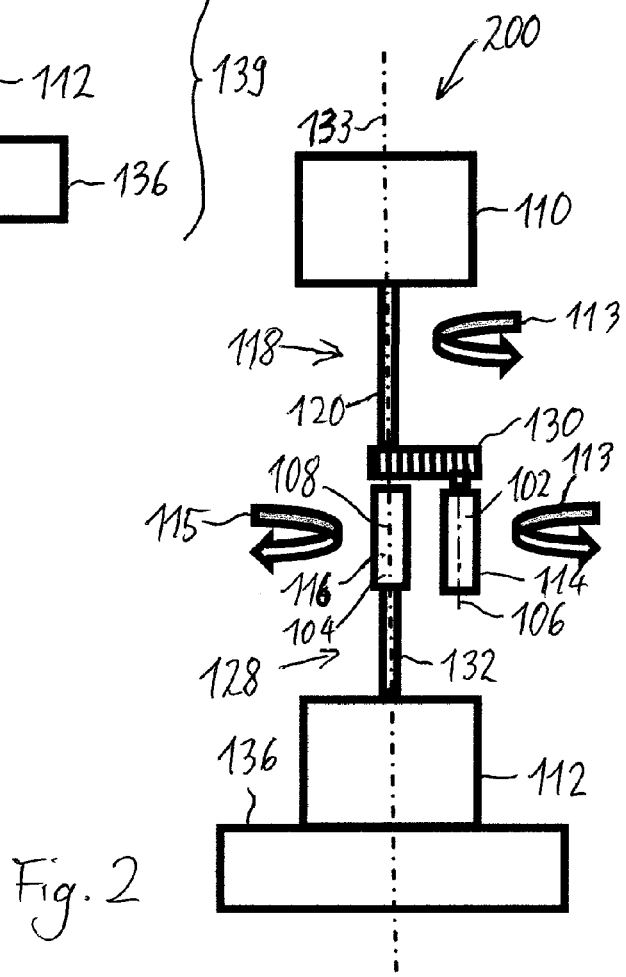
Fig. 1
Fig. 2

DOUBLE-MOTOR RHEOMETER WITH EXTENSION ASSEMBLY

CROSS-REFERENCE TO RELATED APPLICATIONS

The benefit of the filing date of German Patent Application No. 10 2103 207 184.1, filed Apr. 20, 2013, entitled "Double-Motor Rheometer with Extension Assembly," is hereby claimed and the specification thereof incorporated herein in its entirety by this reference.

TECHNICAL FIELD

The invention relates to an extension assembly, to a double motor rheometer, to a method for controlling a double motor rheometer, and to a corresponding computer program.

BACKGROUND

Rheometers are instruments for determining the flow behaviour for example of viscoelastic samples. Known methods for determining the flow behaviour are, for example, rotation tests, creep tests, relaxation tests, and oscillation tests. By means of a rheometer it is possible, for example, to investigate the flow behaviour of fluids and supercooled liquids and also the deformation behaviour of solid bodies.

AT 508 706 B1 relates, in particular, to a method for investigating samples with the use of a rheometer. The rheometer comprises a measuring shaft that is driven by a motor and that carries a first measuring part. Furthermore, the rheometer comprises a measuring gap for the sample, which measuring gap is delimited by the first measuring part and a further measuring part, and comprises a moment detector for detecting the torsional moment of the motor, and a measuring unit for determining the normal force exerted by the sample on the measuring shaft or on the first measuring part. A further measuring shaft, or the axis of rotation of a further measuring shaft, is supported so as to be aligned with the measuring shaft or on the axis of rotation of the measuring shaft, which further measuring shaft is driven by a dedicated further motor and can be affixable or is affixed to the further measuring part. In order to determine the torsional moment exerted by the further motor, a further moment detector is provided. Furthermore, for determining the normal force exerted by the sample on the further measuring part or on the further measuring shaft a further measuring unit is provided.

U.S. Pat. No. 6,691,569 B1 discloses an extensional rheometer, comprising a rotatable primary winding drum and one or more secondary rotatable winding drums. One sample is affixed to the primary winding drum and to each secondary winding drum. Counter rotation of the primary winding drum and each secondary winding drum causes each affixed sample to stretch until rupture. The load response to each primary and secondary winding drum set caused by stretching the sample is measured with a load-sensing device. An environmental control may be provided for testing of samples under various conditions.

US 2012/0234081 A1 discloses an apparatus or a rheometer for determining the extensional properties of a material comprising a first end and a second end. The rheometer comprises first and second rollers gripping the first end of the material. Third and fourth rollers grip the second end of the material. An input shaft rotates the first, second, third and fourth rollers to pull the first and second ends of the material in opposite directions in order to stretch the material.

DE 11 2005 001 096 T5 relates to a system for measuring the extensional characteristics of a sample by means of a stationary cylinder and a movable cylinder, wherein the sample is affixed to the movable cylinder and to the stationary cylinder in such a manner that part of the sample, which part touches neither the movable cylinder nor the stationary cylinder, extends from a tangent of the movable cylinder to a tangent of the stationary cylinder, wherein the movable cylinder is rotated about an axis of the stationary cylinder by rotating a motor drive shaft. Thereby the movable cylinder is rotated about an axis of the movable cylinder, wherein a resistance is generated by the sample when the sample is extended between the movable cylinder and the stationary cylinder as a result of rotation of the movable cylinder about the axis of the stationary cylinder and rotation of the movable cylinder about the axis of the movable cylinder, wherein a torsional moment, acting on the movable cylinder and generated by the resistance, is measured.

SUMMARY

In the light of the disadvantages set out above, there is a need to provide a rheometer with improved characteristics.

This need is met by the subject matter of the independent claims. Advantageous embodiments are described in the dependent claims.

According to an embodiment of a first aspect of the herein disclosed subject matter, an extension assembly is provided that is connected or connectable, in terms of driving (e.g. drivably connected or drivably connectable), to a double motor rheometer (hereinafter also referred to in an abbreviated manner as a "rheometer"), wherein the double motor rheometer comprises a first measuring motor and a second measuring motor, wherein the first measuring motor and the second measuring motor are controllable independently of each other, and wherein each of the first measuring motor and the second measuring motor is provided for determining a torsional moment (torque) generated by the corresponding measuring motor, with the extension assembly comprising: a first sample holding part for holding a first sample portion of a sample; a second sample holding part for holding a second sample portion of the sample; wherein, when the extension assembly is connected, in terms of driving, to the double motor rheometer, the first sample holding part is drivable by the first measuring motor in a rotational movement about a first axis; the second sample holding part is drivable by the second measuring motor in a rotational movement about a second axis; the first axis is arranged so as to be parallel to the second axis; and the first axis is arranged so as to be spaced apart from the second axis so that the sample, held in the first sample portion and in the second sample portion, extends between the first sample holding part and the second sample holding part.

Here the term "rotational movement" does not mandatorily refer to a rotation of 360° or greater, although, depending on the measured samples and on the actual design of the rheometer, such rotational movements are possible. Rather, for example, the rheometer can be configured to allow a maximum pivotal movement of less than 360°, for example of 180°. The rotational movement actually made during a measuring process can comprise very much smaller angular ranges and can, in particular in the case of oscillating movements, involve the smallest angles.

According to an embodiment of a second aspect of the herein disclosed subject matter, a double motor rheometer is disclosed, wherein the double motor rheometer comprises: a first measuring motor; a second measuring motor; and an extension assembly according to one or more embodiments of the herein disclosed subject matter; wherein the first measuring motor and the second measuring motor are controllable independently of each other, and wherein each of the first measuring motor and of the second measuring motor is provided for determining a torsional moment generated by the corresponding measuring motor.

According to an embodiment of a third aspect of the herein disclosed subject matter, a method for controlling a double motor rheometer according to one or more of the embodiments disclosed herein is provided, the method comprising: controlling the first measuring motor and the second measuring motor and thereby effecting an extension of the sample between the first sample holding part and the second sample holding part.

According to an embodiment of a fourth aspect of the herein disclosed subject matter, a computer program for controlling a rheometer is provided, wherein the computer program product is configured to implement the method according to one or more embodiments of the herein disclosed subject matter, when executed on a processor device.

These aspects are based on the fundamental idea that the characteristics of a rheometer can be improved by providing an extension assembly for a double motor rheometer is provided.

According to an embodiment, the first sample holding part and the second sample holding part are each formed by a cylindrical drum; wherein the first axis is a cylinder axis of the first sample holding part; and the second axis is a cylinder axis of the second sample holding part.

According to a further embodiment the extension assembly comprises at least part of a first drive train by way of which the first sample holding part is connected or connectable, in terms of driving, to the first measuring motor; and at least part of a second drive train by means of which the second sample holding part is connected or connectable, in terms of driving, to the second motor; wherein at least one of the first drive train and the second drive train is gearless.

In this document the term "gear mechanism" refers to an assembly of at least two gear wheels, for example toothed wheels, that are coupled, in terms of driving, in order to provide transmission of torsional moment from a gear input shaft to a gear output shaft. Correspondingly, the term "gearless drive train" refers to a drive train that does not comprise a gear mechanism as designated above.

As a result of the gearless design of at least one of the drive trains the accuracy of the rheometer can be improved. In particular, a gearless drive train already makes it possible to carry out oscillatory measurement. Thus the technical prejudice according to which oscillatory measuring is not possible with an extension assembly is overcome. If the gearless drive train alone is subjected to an oscillating torsional moment apparently the gear mechanism contained in the other drive train is surprisingly always under sufficient tension so that the gear backlash has no influence or only little influence on the measuring result, in contrast to corresponding measuring using a conventional rheometer that has a gear mechanism in each drive train.

According to an embodiment the first sample holding part comprises a sample receiving device for affixing the first sample portion of the sample to the first sample holding part, and the second sample holding part comprises a sample receiving device for affixing the second sample portion of the sample to the second sample holding part. As a result of fixing, during rotation of the sample holding part the sample is wound onto the sample holding part.

According to a further embodiment the extension assembly comprises a counterholding element that is arranged so as to be spaced apart from the first sample holding part in order to receive the first sample portion between the first sample holding part and the counterholding element. In this manner the sample is not wound onto the first sample holding part but instead is transported-through between the first sample holding part and the counter element.

According to an embodiment the method comprises controlling the first measuring motor and the second measuring motor in order to impose an extension profile that oscillates over time to the sample between the first sample holding part and the second sample holding part.

According to a further embodiment the method comprises: controlling the first measuring motor and the second measuring motor in order to impose a combined extension profile comprising extension and oscillation to the sample between the first sample holding part and the second sample holding part. As a result of the accuracy achievable by the present exemplary embodiments, even complex extension profiles and/or complex movement profiles of the sample holding parts can be achieved. This applies all the more so to sample holding parts that are connected to their associated measuring motor by way of a gearless drive train.

According to an embodiment, for at least one of the first measuring motor and the second measuring motor a fastening device is provided by means of which the corresponding measuring motor can be affixed in at least two different positions in a direction transversely to the first axis. This results in two different positions of the measuring axes of the rheometer relative to each other. The measuring axis or the rotational axis of the measuring shaft driven by the measuring motor is identical to the rotational axis of the associated measuring motor. According to an embodiment the offset of the two measuring shafts of the measuring motors relative to each other takes place by offsetting at least one of the two measuring motors by way of installation in a second defined motor position. Affixing the at least one measuring motor in the second motor position can, for example, take place by screws, alignment pins, clamping fasteners or the like.

According to a further embodiment the offset of the at least one measuring motor takes place by displacing (shifting) this measuring motor along guide devices such as rails, guides, etc.

According to an embodiment the actual position of the two measuring shafts relative to each other is determined by length measuring. To this end the rheometer can, for example for displacing the measuring motor, comprise a stepper motor, a spindle with an angle encoder, etc. As an alternative, pure length measuring devices can be provided that determine the actual relative positions of the two measuring shafts. For example, the length measuring device can be attached to one of the measuring motors and can be configured to measure the distance of the other measuring motor from the length measuring device. Because the measuring shafts have a defined position relative to the measuring motor, the distance between the measuring shafts is thus also defined.

According to a further embodiment the rheometer comprises a control device for controlling the first measuring motor and the second measuring motor and thus causes an extension of the sample between the first sample holding part and the second sample holding part.

Here, controlling can take place in an open control loop, i.e. without the use of feedback signals (open loop control).

Preferably, however, controlling takes place with the use of feedback signals, i.e. in a closed control loop (closed loop control). As a result of such a closed loop control it is possible to achieve a higher accuracy. Furthermore, measuring modes can be defined that cannot be implemented in an open control loop (e.g. constant extensional rate; to this end the force needs to be reduced in line with the reduction in the sample cross section).

According to an embodiment, controlling the first and the second measuring motors comprises: controlling the first measuring motor in order to rotate the first measuring motor in a first direction of rotation; controlling the second measuring motor in order to rotate the second measuring motor in a second direction of rotation; wherein the second direction of rotation is against the first direction of rotation (counter-rotation) or in the first direction of rotation (co-rotation).

According to an embodiment the control device is configured for determining a torsional moment generated by the first measuring motor and/or a torsional moment generated by the second measuring motor. The torsional moment can, for example, be derived from the current consumption of the corresponding measuring motor, as is known to a person skilled in the art.

According to a further embodiment the method further comprises: determining a first torsional moment generated by the first measuring motor; determining a second torsional moment generated by the second measuring motor; calculating an average value from the first torsional moment and the second torsional moment; and controlling at least one of the first measuring motor and the second measuring motor in response to the average value. As a result of average value calculation the accuracy of determining the torsional moment and thus determining the force acting on the sample is improved. In this manner the characteristics of the rheometer can be improved.

In the context of the present invention, any reference to a computer program is synonymous to a reference to a program element, a computer program product and/or a computer-readable medium comprising instructions for controlling a computer system in order to coordinate the mode of operation of a system or of a method in a suitable manner in order to achieve the effects linked to the embodiments of a method that are disclosed herein.

According to an embodiment the control device comprises at least one processor that is configured in such a manner that with the execution of the computer program the method-related steps described above can be carried out.

For example, a program element (computer program element) causes the execution of method-related steps according to one or more embodiments when it is executed on a processor.

The computer program can be implemented as a computer-readable instruction code in any suitable programming language, for example in JAVA, C++ etc. The computer program can be stored on a computer-readable storage medium (CD-ROM, DVD, removable drive, volatile or non-volatile memory, built-in memory/processor etc.). The instruction code can program a computer or other programmable devices, in particular the control device, in such a manner that the desired functions are carried out. Further, the computer program can be provided in a network, for example on the internet, from which it can be downloaded by a user when required.

The control device can be implemented by means of a computer program, i.e. software, or by means of one or more specific electrical circuits, i.e. in hardware or in any desired hybrid form, i.e. by means of software components and hardware components.

Below, exemplary embodiments of the herein disclosed subject matter are described, wherein, for example, reference is made to a method for controlling a double motor rheometer, to an extension assembly that is connected or connectable, in terms of driving, to a double motor rheometer, and to a double motor rheometer. It should be emphasised that of course any combination of features of various aspects, embodiments and examples is possible. In particular, some embodiments are described with reference to a method, while other embodiments are described with reference to a device. Yet other embodiments are described with reference to an extension assembly while other embodiments are described with reference to a double motor rheometer. However, a person skilled in the art will take from the description presented above and below, from the claims and from the drawings that unless otherwise stated, features of various aspects, embodiments and examples can be combined at will. For example, even a feature that relates to a method can be combined with a feature that refers to a device. Furthermore, with a feature that refers to a method, a corresponding feature that refers to a device is considered to be disclosed and vice versa.

Further advantages and features of the present invention are stated in the following exemplary description of presently preferred embodiments, wherein the invention is not, however, limited to these embodiments. The individual figures of the drawings of this application are merely to be considered to be diagrammatic and not to scale.

BRIEF DESCRIPTION OF THE DRAWINGS

FIG. 1 shows a double motor rheometer according to embodiments of the herein disclosed subject matter.

FIG. 2 shows a double motor rheometer 200 according to embodiments of the herein disclosed subject matter.

DETAILED DESCRIPTION

Figure 3:
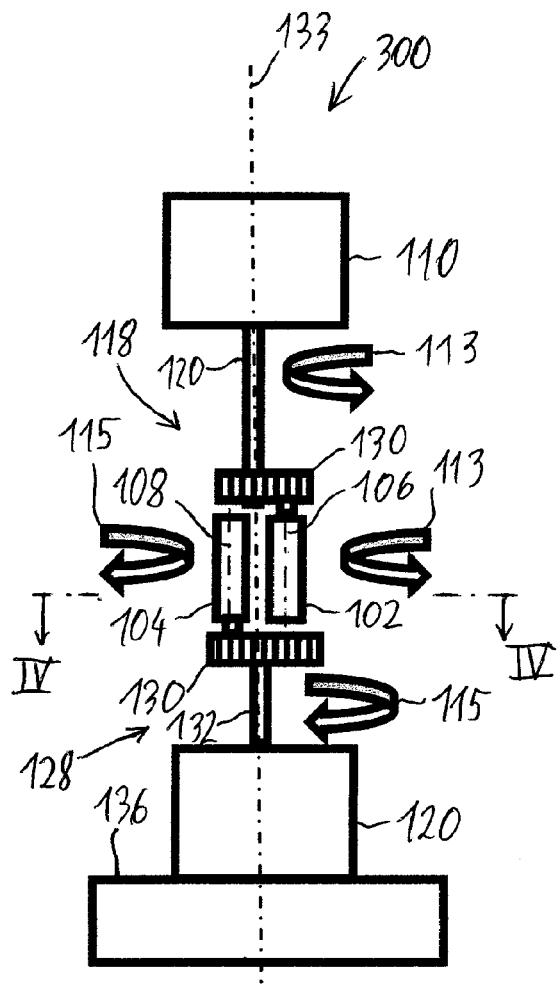
FIG. 3 shows a further double motor rheometer according to embodiments of the herein disclosed subject matter.

FIG. 1 shows a double motor rheometer according to embodiments of the herein disclosed subject matter.

The double motor rheometer 100 comprises a first sample holding part 102 for holding a first sample portion of a sample not shown in FIG. 1. Furthermore, the double motor rheometer 100 comprises a second sample holding part 104 for holding a second sample portion of the sample. The first sample holding part 102 and the second sample holding part 104 each are rotatable about a first axis 106 or about a second axis 108, respectively. In this embodiment the first axis 106 is arranged so as to be parallel to the second axis 108. Furthermore, the first axis 106 is arranged so as to be spaced apart from the second axis 108 so that the sample (not shown in FIG. 1) held in the first sample portion and in the second sample portion extends between the first sample holding part 102 and the second sample holding part 104.

Furthermore, the double motor rheometer 100 comprises a first measuring motor 110 and a second measuring motor 112 that are controllable independently of each other. The first measuring motor 110 is provided for driving the first sample holding part 102. The second measuring motor 112 is provided for driving the second sample holding part 104. According to an embodiment the double motor rheometer 100 is configured so that the first measuring motor 110 drives the first sample holding part 102 in a rotational movement 113 about the first axis 106, and the second measuring motor 112 drives the second sample holding part 104 in a rotational movement 115 about the second axis 108.

The first measuring motor 110 is provided for determining the torsional moment generated by the first measuring motor 110. Analogously the second measuring motor 112 is provided for determining a torsional moment generated by the second measuring motor 112. Determining the torsional moment generated by the measuring motor 110, 112 can, for example, take place by measuring the current consumption of the measuring motor 110, 112. However, alternative methods for determining the torsional moment generated by the corresponding measuring motor 110, 112 are equally suitable.

According to an embodiment shown in FIG. 1, the first sample holding part 102 is formed by a cylindrical drum, and the second sample holding part 104 is likewise formed by a cylindrical drum. Here the first axis 106 is a cylinder axis of the first sample holding part 102, and the second axis 108 is a cylinder axis of the second sample holding part 104. By fastening the sample (not shown) to the drums, each drum serves to hold the sample and also to wind the sample onto a generated surface 114, 116 of the drum during rotation of the drum about the first axis 106 or about the second axis 108.

According to an embodiment the first sample holding part 102 is connected to the first measuring motor 110 by a first drive train 118. According to an embodiment the first drive train 118 is configured so as to be gearless. For example, the first drive train 118 can be formed by a first measuring shaft 120 that extends from the first measuring motor 110 to the first sample holding part 102. The first measuring shaft 120 thus provides a direct connection, in terms of driving, of the first measuring motor 110 to the first sample holding part 102. According to an embodiment the first measuring shaft 120 can be a continuous single-piece measuring shaft (not shown). According to another embodiment the first measuring shaft 120 can comprise a coupling by means of which the first measuring motor 110 is connectable, in terms of driving, to the first sample holding part. According to a further embodiment the coupling 122 allows a separation of a measuring shaft part 124 on the side of the motor from a measuring shaft part 126 on the side of the sample holding part. In this manner the first sample holding part 102 can be exchanged for another measuring device. According to another embodiment the coupling 122 can be arranged directly on the first sample holding part 102 so that the measuring shaft part 126 on the side of the sample holding part can be omitted.

According to a further embodiment the second sample holding part 104 is connected, in terms of driving, by a second drive train 128 to the second motor 112. According to an embodiment at least one of the first drive train and the second drive train, for example the second drive train 128, comprises a gear mechanism 130, as is shown in FIG. 1. According to an embodiment the rheometer 100 comprises a second measuring shaft 132 to which the gear mechanism 130 is connected, in terms of driving. According to an embodiment the gear mechanism 130 provides a lateral offset of the second axis 108 of the second sample holding part 104 relative to the second measuring shaft 132. In this manner embodiments of the herein disclosed subject matter can be implemented in a rheometer in which the first measuring shaft 120 and the second measuring shaft 132 are arranged so as to be aligned, as is shown in FIG. 1. The gear mechanism 130 thus provides a distance d between the first sample holding part 102 and the second sample holding part 104.

According to an embodiment the gear mechanism 130 comprises a coupling 134 by means of which the gear mechanism 130 is connectable, in terms of driving, to the second measuring shaft 132. According to another embodiment the coupling 134 can be arranged between two parts of a two-part second measuring shaft, analogous to the coupling 122, shown in FIG. 1, of the first drive train 118.

The couplings 122, 134 can be formed by means of suitable coupling elements on the parts to be coupled. The couplings can, for example, comprise quick-action closures (if applicable with locking devices) and/or magnetic couplings. According to an embodiment the measuring shafts 120, 122 are supported by means of suitable (in particular low-friction or non-friction) bearings, for example by means of air bearings or magnetic bearings.

According to an embodiment the first measuring shaft 120 and the second measuring shaft 132 are arranged so as to be aligned, thus defining a measuring axis 133, as shown in FIG. 1.

According to an embodiment the first measuring motor 110 and the second measuring motor 112 are fastened to a support 136, wherein for the sake of clarity the mechanical connection between the support 136 and the first measuring motor 110 is not shown in FIG. 1.

Generally speaking, according to an embodiment, of the drive train 118, 128 a part that extends between the coupling 122, 134 of the drive train 118, 128 and the corresponding sample holding part 102, 104 forms part of an extension assembly 135 that forms an exchangeable part of the rheometer 100. For example, according to an embodiment the extension assembly 135 comprises the measuring shaft part 126 on the side of the sample holding part, the first sample holding part 102, the second sample holding part 104 and the gear mechanism 130. The rest of the rheometer 100 forms a rheometer base 137, 139 of the rheometer 100. According to an embodiment, by opening the coupling 122 in the first drive train 118 and opening the coupling 134 in the second drive train 128 the extension assembly 135 can be removed from the rheometer base 137, 139. For example, the extension assembly 135 can be adapted to be marketed and sold as additional equipment for a rheometer with another measuring device (for example plates).

For example, according to an embodiment the following features can provide compatibility of the extension device 135 with a given rheometer base 137, 139: (i) compatible coupling elements on the side of the extension assembly, which coupling elements match the coupling elements on the side of the measuring motor of the rheometer and together with the aforesaid form the couplings 122, 134; and, if required, (ii) a suitably configured gear mechanism that provides a desired distance d between the first sample holding part 102 and the second sample holding part 104.

FIG. 2 shows a double motor rheometer 200 according to embodiments of the herein disclosed subject matter.

The double motor rheometer 200 in FIG. 2 is configured similarly to the rheometer 100 shown in FIG. 1, except that the gear mechanism 130 is now arranged in the first drive train 118 so as to laterally displace the first sample holding part 102 relative to the first measuring shaft 120 and arrange it so as to be spaced apart from the second sample holding part 104 which according to an embodiment is directly connected, in terms of driving, to the second measuring shaft 132 and is aligned with said measuring shaft 132, as is shown in FIG. 2.

FIG. 1 and FIG. 2 thus show examples of an embodiment in which at least one sample holding part 102, 104 is aligned with its associated measuring shaft 120, 132.

According to an embodiment the couplings 122 and 134, as described with reference to FIG. 1, can be omitted, as is shown, for example, in FIG. 2.

The remaining features of the rheometer 200 correspond to those of the rheometer 100 of FIG. 1 and comprise identical reference characters. A detailed description of these features is therefore not repeated.

FIG. 3 shows a further double motor rheometer according to embodiments of the herein disclosed subject matter.

The double motor rheometer 300 in FIG. 3 is configured in a manner similar to that of the double motor rheometers 100 and 200 that are shown in FIG. 1 and FIG. 2. However, unlike rheometers 100 and 200, according to an embodiment the rheometer 300 comprises a gear mechanism 130 both in the first drive train 118 and in the second drive train 128. As already described with reference to FIG. 1 and FIG. 2 the gear mechanism 130 in each case serves to laterally offset the corresponding sample holding part 102, 104 relative to its measuring shaft 120, 132. In this manner a symmetrical arrangement of the sample holding part 102, 104 relative to the measuring axis 133 is achieved.

The remaining features of the rheometer 300 correspond to those of the rheometer 100 of FIG. 1 and comprise identical reference characters. A detailed description of these features is therefore not repeated.

Figure 4:
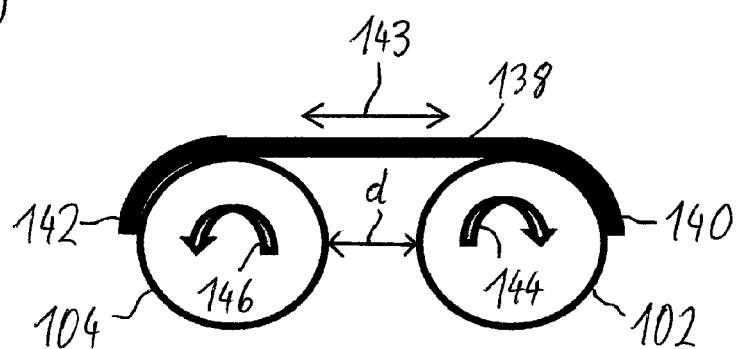
FIG. 4 shows a cross section of a double motor rheometer according to embodiments of the herein disclosed subject matter, in particular a cross-sectional view of the rheometer 300 of FIG. 3 along the line IV-IV.

FIG. 4 shows a cross section of a double motor rheometer according to embodiments of the herein disclosed subject matter, in particular a cross-sectional view of the rheometer 300 of FIG. 3 along the line IV-IV.

FIG. 4 shows, in particular, the first sample holding part 102 and the second sample holding part 104 that are arranged so as to be spaced apart from each other at a distance d. According to an embodiment a sample 138 is affixed in a first sample portion 140 to the first sample holding part 102, for example in a sample receiving device. The term "sample receiving device" can, for example, refer to a clamping device for clamping the sample to the sample holding part 102 as is known to a person skilled in the art. In a second sample portion 142 the sample 138 is affixed to the second sample holding part 104, for example also in a sample receiving device. As a result of counter rotation of the sample holding parts 102, 104 the sample 138 is extended (indicated by the double arrow 143) between the first sample holding part 102 and the second sample holding part 104. Correspondingly, according to an embodiment shown in FIG. 4 the direction of rotation 144 of the first sample holding part 102 is opposite to the direction of rotation 146 of the second sample holding part 104.

Figure 5:
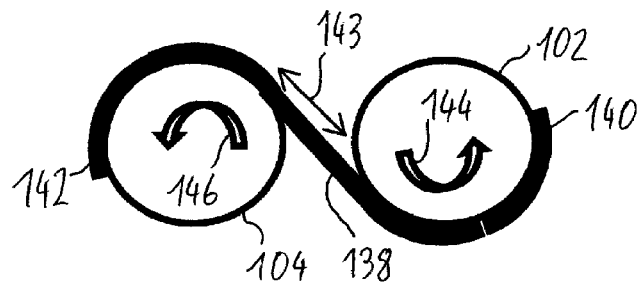
FIG. 5 shows the cross section of the double motor rheometer of FIG. 4 with alternative sample placement according to embodiments of the herein disclosed subject matter.

FIG. 5 shows the cross section of the double motor rheometer of FIG. 4 with alternative sample placement according to embodiments of the herein disclosed subject matter.

In particular, in FIG. 5 the sample 138 is placed transversely between the first sample holding part 102 and the second sample holding part 104 so that for extending the sample 138 the first sample holding part 102 and the second sample holding part 104 can rotate in the same direction while nevertheless pulling the sample portion between the first sample holding part 102 and the second sample holding part 104 in opposite directions, thus extending it. Correspondingly, according to an embodiment as shown in FIG. 5, the direction of rotation 144 of the first sample holding part 102 is the same as the direction of rotation 146 of the second sample holding part 104.

According to an embodiment the gear mechanism 130 reverses the direction of rotation of the associated measuring shaft 120, 132. According to an embodiment this is taken into account by a control device that controls the measuring motors 110, 112 in order to set the direction of rotation of the corresponding measuring motor 110, 112 according to the placement of the sample 138 between the first sample holding part 102 and the second sample holding part 104.

FIG. 4 and FIG. 5 represent a cross-sectional view of the rheometer 300 in FIG. 3. However, it is understood that a corresponding cross-sectional view of the rheometers 100, 200 in FIG. 1 and FIG. 2 according to an embodiment can be identical to that shown in FIG. 4 and FIG. 5. By decoupling the two sample holding parts (i.e. by driving each sample holding part by means of a separate measuring motor) the potential for errors or inaccuracies can be reduced. In particular, in this manner it is possible for the first time to carry out oscillatory measurements with an extension assembly in which the sample extends between two rotating sample holding parts.

As a result of the options of the double-motor rotational-cylinder rheometer according to embodiments of the herein disclosed subject matter, it is possible, for example, to record extension profiles with identical rotational speeds of the two measuring motors 110, 112 and with measuring the effective torsional moments on the upper and/or lower measuring axis 120, 132. In this manner on both sample holding parts 102, 104 exactly the same rate of extension can be specified. Moreover, any desired movement profiles of the sample holding parts 102, 104, for example with different rotational speeds, can be specified. In particular, complex movement profiles can be achieved. For example, it is possible to superimpose on a defined rate of extension (i.e. a defined rotational speed of the sample holding parts 102, 104) an extension that oscillates over time (temporally oscillating extension), i.e. the torsional moment generated by the corresponding measuring motor 110, 112 oscillates over time. Oscillation can be set on one sample holding part 102 or 104, or on both sample holding parts 102, 104. According to an embodiment only that sample holding part is oscillatorily driven that does not comprise a gear mechanism in its associated drive train. Conversely, according to an embodiment a sample holding part whose associated drive train comprises a gear mechanism is not oscillatorily driven. If in such a case a gear mechanism is arranged only in one drive train, this at most has little effect on oscillatory measuring because in this case this gear mechanism is subjected to permanent tensile loading even during oscillatory extension, and the gear backlash has thus no influence, or at most little influence, on oscillatory measuring. Depending on the sample placement, the sample holding parts 102, 104 can be rotated in the same direction (co-rotation) or in opposite directions (counter-rotation) in order to cause extension of the sample.

While each of the above-mentioned double motor rheometers 100, 200, 300 comprises a gear mechanism 130 in at least one drive train 118, 128, according to a further embodiment both drive trains can be gearless.

Figure 6:
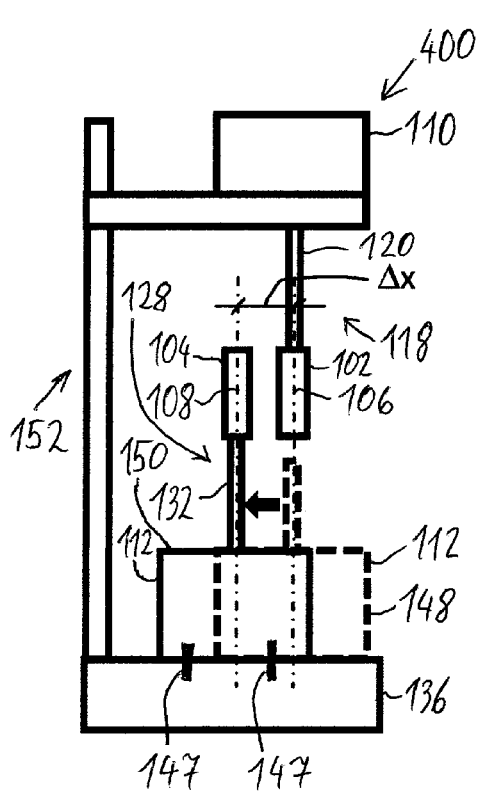
FIG. 6 shows a lateral view of a further double motor rheometer 400 according to embodiments of the herein disclosed subject matter.

FIG. 6 shows a lateral view of a further double motor rheometer 400 according to embodiments of the herein disclosed subject matter.

According to an embodiment for at least one of the first measuring motor 110 and the second measuring motor 112 a fastening device 147 is provided, by means of which the corresponding measuring motor can be affixed in at least two different positions in a direction transversely to the first axis. For example such a fastening device can be provided for the second measuring motor, as is shown in FIG. 6. According to an embodiment, in a first position 148 (in FIG. 6 shown in dashed lines) the measuring shafts 120 and 132 are positioned so as to be aligned, and in a second position 150 (in FIG. 6 shown in solid lines) the measuring shafts 120 and 132 are arranged at a distance Δx from each other.

According to an embodiment the fastening device 147 is formed by screws, through-holes in the second measuring motor 112 and associated threaded holes in the support 136. In particular, two sets of threaded holes can be formed in the support 136 in order to make it possible to affix the second measuring motor 112 in two different positions. According to other embodiments the fastening device 147 can comprise any desired suitable elements such as alingment pins, screws, clamping fasteners, bolts etc.

According to an embodiment the rheometer 400 comprises a tripod 152 to which the first measuring motor 110 is affixed. According to an embodiment the tripod 152 can be adjustable, for example height-adjustable, so that a distance can be set between the first measuring motor 110 and the second measuring motor 112. According to other embodiments the distance between the first measuring motor 110 and the second measuring motor 112 can be fixed. According to an embodiment the tripod 152 is affixed to the support 136.

As a result of the arrangement of the measuring shafts 120, 132 at a distance Δx from each other the sample holding parts 102, 104 can both be arranged so as to be aligned with the associated measuring shaft 120, 132. For example, in this manner a gear mechanism in the first drive train 118 and in the second drive train 128 can be omitted, as is shown in FIG. 6.

Figure 7:
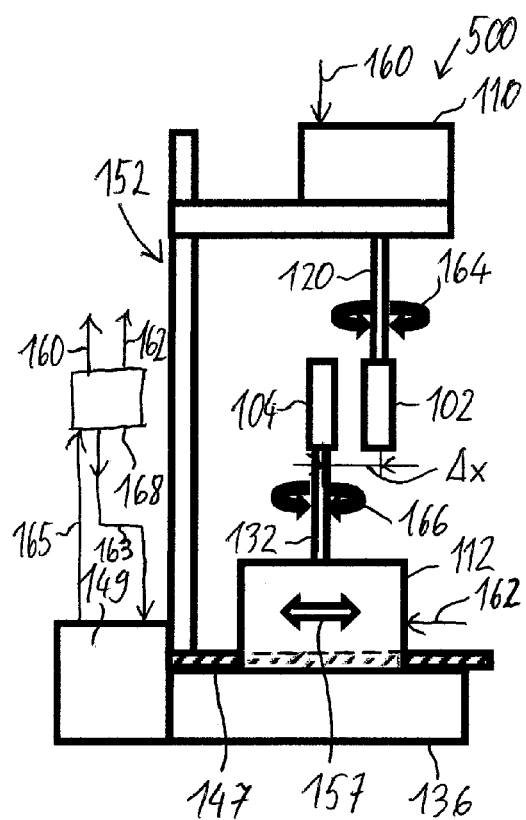
FIG. 7 shows a lateral view of a further double motor rheometer 500 according to embodiments of the herein disclosed subject matter.

FIG. 7 shows a lateral view of a further double motor rheometer 500 according to embodiments of the herein disclosed subject matter.

According to an embodiment the fastening device 147 is configured in such a manner that the at least one measuring motor 112 is displaceable transversely to the first axis and can be affixed in at least two different positions. The fastening device 147 can be adapted to allow displacement of the corresponding measuring motor 112 perpendicularly to the first axis 106. Such displaceability is indicated in FIG. 7 by means of the double-headed arrow 154. This displaceability can be provided by any suitable elements, for example a guide or an adjustable displacement device 149, for example a linear drive, stepper motor, spindle gear with angle encoder, etc. as known, for example, also for providing height adjustment of the tripod 152. Such a displacement device can, for example, also provide a distance value that is a measure of the distance between the first measuring shaft 120 and the second measuring shaft 132, and can thus serve as a distance measuring device. According to an embodiment the displacement device 149 is controlled by the control device 168 by means of control signals 163. According to a further embodiment the displacement device 149 provides the control device 168 with distance signals 165, which correspond to Δx. According to an embodiment the first measuring motor 110 and the second measuring motor 112 are adapted, depending on control signals 160, 162, to drive the first sample holding part 102 and the second sample holding part 104 into a rotational movement in a settable direction of rotation as indicated at 164 in relation to the first measuring motor 110 and at 166 in relation to the second measuring motor 112. Because of the distance Δx of the first measuring axis 120 and of the second measuring axis 132 the rheometers in FIG. 6 and FIG. 7 can also be referred to as orthogonal rheometers.

As a result of the gearless design of both drive trains 118, 128 the accuracy of the rheometers 400, 500 is significantly improved when compared to known rheometers. It is therefore possible, in particular, to implement complex movement profiles of the sample holding parts 102, 104. Here, control of the first measuring motor 110 takes place by means of a control signal 160 that is provided by a control device 168, as explained above. The second measuring motor 112 is controlled by means of a second control signal 162 that is provided by the control device 168. According to an embodiment the control device 168 is configured for controlling the first measuring motor 110 and the second measuring motor 112 to thereby effect extension of the sample between the first sample holding part 102 and the second sample holding part 104. According to an embodiment the control signals 160, 162 are provided, in a closed control loop, by the control device 168 in response to a feedback signal. The feedback signal can, for example, comprise values relating to one or more of the following parameters: rotation angle of the first measuring motor 110, rotation angle of the second measuring motor 112, angular speed of the first measuring motor 110, angular speed of the second measuring motor 112, torsional moment exerted by the first measuring motor 110, torsional moment exerted by the second measuring motor 112. It goes without saying that the above-mentioned parameters are only examples of feedback parameters, and that the provision of the control signals 160, 162 can be based on additional or alternative other feedback parameters. The torsional moment of the measuring motors can, for example, be determined from the current that is supplied to the corresponding measuring motor, for example by way of calibration tables or calibration functions. Since a person skilled in the art is familiar with this, no further description relating to determining suitable feedback parameters is provided. According to an embodiment by way of the control device 168, a torsional moment relating to the first measuring motor 110 and/or to the second measuring motor 112 may be specified.

According to an embodiment the first measuring motor 110 and the second measuring motor 112 are controlled by the control device 168 in order to impose an extension profile that oscillates over time on the sample between the first sample holding part and the second sample holding part. Because of the absence of gear backlash, in particular the double motor rheometers 400 and 500 of FIG. 6 and FIG. 7 are well suited to this. In particular, in these two rheometers exactly symmetrical extension of the sample can take place, even in the case of oscillatory extension, because both the first sample holding part 102 and the second sample holding part 104 can be subjected to a very precise oscillatory torsional moment.

Furthermore, because of the precise implementable movement profiles of the first sample holding part and of the second sample holding part, the herein described rheometers make it possible to specify minute tensile stress (force specification) in an extension assembly with rotating sample holding parts, which is not possible with the use of known extension assemblys with rotating sample holding parts because in those designs the driving mechanism is always implemented by way of a mechanical gear mechanism that in the case of the most minute rates results in great inaccuracies as a result of gear backlash. In contrast to this, in a double motor rheometer according to embodiments of the herein disclosed subject matter, rotation takes place by means of two measuring motors. According to an embodiment, in this design both measuring motors can determine and/or specify the effective torsional moments.

Figure 8:
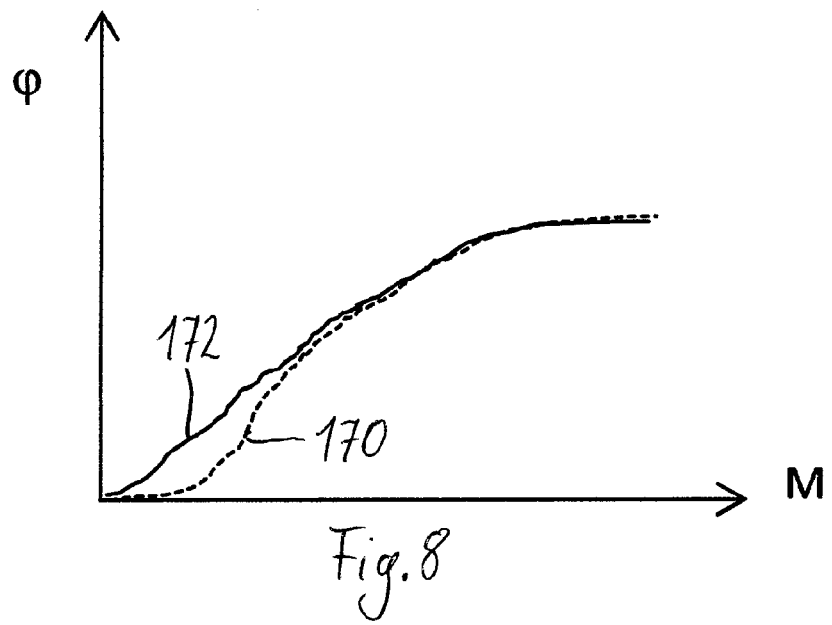
FIG. 8 shows a diagram of a rheometer according to embodiments of the herein disclosed subject matter and of a conventional rheometer, which diagram shows the rotation angle φ of the sample holding parts relative to the actually effective torsional moment M.

FIG. 8 shows a diagram relating to a rheometer according to embodiments of the herein disclosed subject matter and to a conventional rheometer, which diagram shows the rotation angle $\phi$ of the sample holding parts relative to the actually effective torsional moment M. In this diagram the rotation angle $\phi$ is proportional to the extension of the sample between the two sample holding parts 102, 104. The dashed line 170 in FIG. 8 shows the gradient of the rotation angle $\phi$ relative to the actually effective torsional moment M in a rheometer that comprises a single motor for driving two rotatable sample holding parts, wherein both sample holding parts are driven by the only motor by way of a gear mechanism. In contrast to this, the solid line 172 in FIG. 8 shows the rotation angle $\phi$ relative to the actually effective torsional moment M in relation to a double motor rheometer that is gearless in both drive trains 118, 128 as has been described, for example, with reference to FIG. 6 and FIG. 7. The diagram shows that in the conventional rheometer 170 in the start-up region, in the case of small angles the force effect is clearly delayed as a result of the gear backlash.

However, not only the greater accuracy of the double motor rheometer according to embodiments of the herein disclosed subject matter, but also the possibility of precisely symmetrical extension of the sample provides new application options. For example, in such a case it is possible to combine extensional rheology with other investigations, wherein measurements can take place on the centre, which does not move, of the extended sample. This makes it possible to implement a combination of investigation methods, which combination has hitherto not been possible in this form. As a result of the sample extending between the first sample holding part and the second sample holding part the extensional rheometer ensures good access of the sample in this region. Since in such an embodiment the centre of the extended sample does not move, further analysis methods can reliably be provided for, for example microscopy, small-angle light scattering, SALS; small-angle neutron scattering, SANS; small-angle X-ray scattering, SAXS; birefringence, etc.

Figure 9:
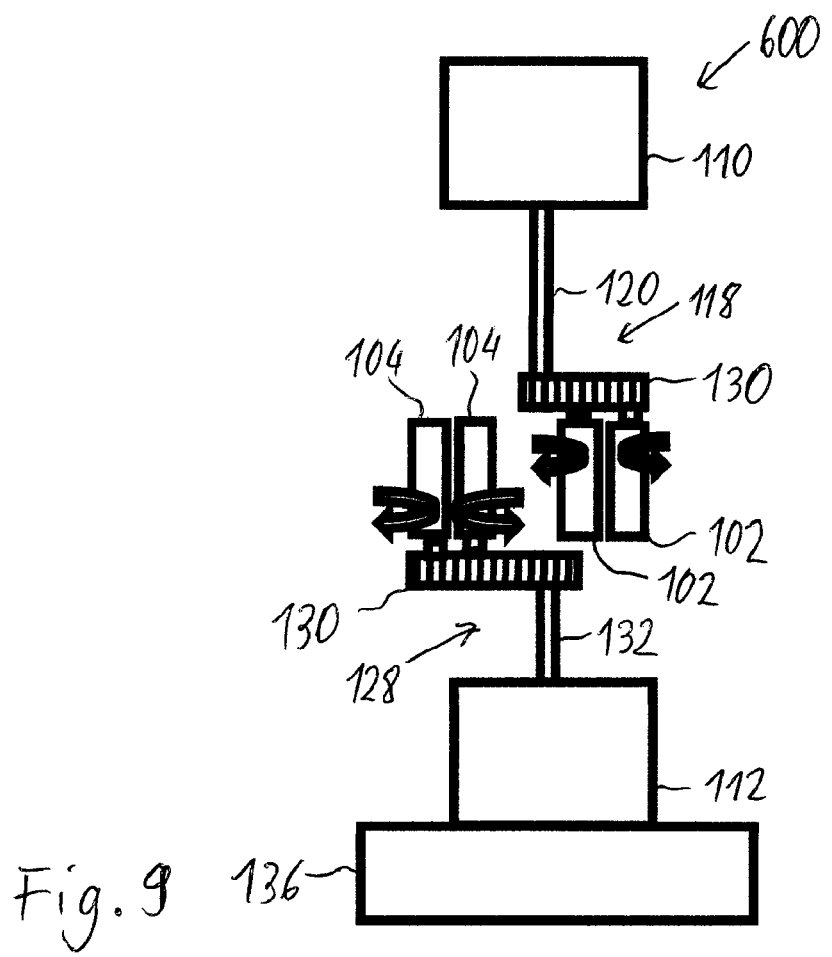
FIG. 9 shows a further double motor rheometer 600 according to embodiments of the herein disclosed subject matter.

FIG. 9 shows a further double motor rheometer 600 according to embodiments of the herein disclosed subject matter.

The double motor rheometer 600 shown in FIG. 9 comprises two aligned measuring shafts 120 and 132. In contrast to rheometers 100, 200, 300, 400 and 500, however, two sample holding parts are provided for holding each sample portion. Of these two sample holding parts, which are associated with a sample portion, one acts as a counterholding element, which is arranged so as to be spaced apart from the sample holding part, for receiving the sample portion between the sample holding part and the counterholding element. Thus the rheometer 600 comprises two first sample holding parts 102 for holding a first sample portion of a sample (not shown in FIG. 9). Furthermore, the rheometer 600 comprises two second sample holding parts 104 for holding a second sample portion of the sample. The two first sample holding parts receive the sample between themselves and pull the first sample portion by means of rotation of the two first sample holding parts in opposite directions. Correspondingly the two second sample holding parts 104 hold the second sample portion between themselves and pull it with rotation of the two second sample holding parts 104 in opposite directions. Such a configuration of two pairs of sample holding parts has been described by Maya in US 2012/234081 A1. By providing two separate measuring motors 110, 112 according to embodiments of the herein disclosed subject matter, the accuracy of rotation of the first sample holding parts 102 and the second sample holding parts 104 can be improved, even if according to an embodiment two gear mechanisms 130 are used for this. According to an embodiment each gear mechanism 130 comprises an input that is driven by the measuring shaft 120, 132. Furthermore, according to an embodiment each gear mechanism 130 comprises two outputs that are driven at identical speeds but in opposite directions of rotation for driving the two sample holding parts of interest (first sample holding parts 102 or second sample holding parts 104). By using such a respective gear mechanism 130 in the first drive train 118 and in the second drive train 128 frictional forces are reduced when compared to the solution described by Maya. Since, furthermore, both measuring motors can determine the active torsional moments, by averaging the torsional moments generated by the first measuring motor 110 and the second measuring motor 112 the accuracy of the rheometer can be still further improved.

IN SUMMARY

An extension assembly is described that is connected or connectable, in terms of driving, to a double motor rheometer. The double motor rheometer comprises a first measuring motor and a second measuring motor, wherein the first measuring motor and the second measuring motor are controllable independently of each other, and wherein each of the first measuring motor and the second measuring motor is provided for determining a torsional moment generated by the corresponding measuring motor. The extension assembly comprises: a first sample holding part for holding a first sample portion of a sample, and a second sample holding part for holding a second sample portion of the sample. When the extension assembly is connected, in terms of driving, to the double motor rheometer the first sample holding part is drivable by the first measuring motor in a rotational movement about a first axis, and the second sample holding part is drivable by the second measuring motor in a rotational movement about a second axis. Furthermore, in this case the first axis is arranged so as to be parallel to the second axis, and the first axis is arranged so as to be spaced apart from the second axis so that the sample held in the first sample portion and in the second sample portion extends between the first sample holding part and the second sample holding part.

When compared to conventional rheometer designs, an extension assembly according to embodiments of the herein disclosed subject matter opens up entirely new possibilities. From now on it is possible to measure and to rotate on both sample holding parts independently of each other. According to an embodiment the herein disclosed subject matter makes it possible for the sample to be clamped to and/or wound onto two sample holding parts (e.g. extension drums/jaws/rollers), and for the two sample holding parts to be driven independently of each other, each by one of the measuring motors of the rheometer. According to an embodiment the two sample holding parts are not coupled by way of a gear mechanism as is the case in the known extension assemblys. If the measuring axes are left in a position in which they are aligned relative to each other, at least one of the sample holding parts still needs to be provided with a gear mechanism in order to displace the axis of the sample holding part from the position of the measuring shaft of the measuring motor by Δx and in this manner obtain two parallel sample holding parts.

Further advantages of embodiments of the herein disclosed subject matter are as follows:

Constant Tensile Stress

In particular in the case of torsional moment profiles simultaneously take into account the dimensions of the sample (e.g. by concurrent optical examination and evaluation of the sample cross section with the use of a microscope or a CCD camera), due to the good reproducibility of the specifications and the direct effect on the sample holding parts, the tensile stress can be regulated so that despite the changing sample cross section during extension, the tensile stress is kept constant. During extension the sample becomes thinner and thinner. Consequently, if constant tensile stress is to be achieved in a sample, the rate of extension needs to be adjusted to the sample cross section that diminishes as a result of extension; the specified moment needs to become correspondingly smaller.

Oscillation

The hitherto commonly used gear mechanism arrangements are not suitable for carrying out oscillation tests. Thus for the first time the possibility of oscillation of extension samples with the use of rotational rheometers opens up. Due to the temperature chambers customary in the rheometers, which temperature chambers can bring the clamped-in sample to temperature over a wide temperature range and allow high-precision setting of temperature profiles, it also becomes possible to carry out dynamic-mechanical thermal analyses with this extension assembly, which analyses have hitherto required the use of special devices (DMTA measurements in extension).

LAOS Experiments

Especially for investigating non-linear phenomena on polymers, oscillation measurements with great amplitudes are necessary, which are presently available only to a limited extent in special extensional rheometers. The present extension assembly is also suitable for carrying out large amplitude oscillatory shear (LAOS) experiments. These experiments are often evaluated with the use of FT-rheology, in which the measured values are subjected to Fourier transformation. For the most part this requires large shear amplitudes in order to achieve non-linear conditions. First experiments on this topic have already been carried out, for example, by Krieger et. al. ("A rheometer for oscillatory studies of nonlinear fluids", Rheol. Acta 12, 567-571 (1973)). The FT-rheology applied in these studies is characterised by particularly high sensitivity and a very good signal-to-noise ratio. If necessary the mathematical steps required for evaluation can be made available directly in the control device 168.

Superposition Rheology

Extension superimposed by oscillation provides new possibilities in terms of study profiles. This can, for example, be achieved in that a measuring motor is rotated, while the other measuring motor is oscillated. In this manner studies on superposition rheology in extension can be carried out. As a result of extension, structural changes can be induced in the sample whose elastic behaviour is observed or measured depending on the applied extension or rate of extension with oscillation.

Complex Profiles

The assembly makes it possible to alternate at will between rotation and oscillation: e.g. extension to a certain angle, Hencky strain tests and measuring the relaxation with oscillation. In an embodiment in which neither of the drive trains 118, 128 has a gear mechanism, and thus both sample holding parts can be moved quasi-without any play and without any friction, changes are possible at will between deformation leaps, deformation rates, force specification and also oscillation. It is thus possible to carry out complex study profiles even in extension. All rotation options in counter-rotation and co-rotation with all possible distributions of the rotational speeds are possible.

The invention claimed is:

1. A double motor rheometer, comprising:
   a first measuring motor;
   a second measuring motor; and
   an extension assembly, the extension assembly connected or connectable, in terms of driving, to the first measuring motor and the second measuring motor, wherein the first measuring motor and the second measuring motor are controllable independently of each other, and wherein each of the first measuring motor and the second measuring motor is provided for determining a torsional moment generated by the corresponding measuring motor, the extension assembly including:
   a first sample holding part for holding a first sample portion of a sample;
   a second sample holding part for holding a second sample portion of the sample;
   wherein, when the extension assembly is connected, in terms of driving, to the double motor rheometer, the first sample holding part is drivable by the first measuring motor in a rotational movement about a first axis;
   the second sample holding part is drivable by the second measuring motor in a rotational movement about a second axis;
   the first axis is arranged so as to be parallel to and spaced apart from the second axis so that the sample held in the first sample portion and in the second sample portion extends between the first sample holding part and the second sample holding part; and
   for at least one of the first measuring motor and the second measuring motor a fastening device is provided by which the corresponding measuring motor is affixable in at least two different positions in a direction transverse to the first axis.

2. The double motor rheometer according to claim 1, wherein the first sample holding part and the second sample holding part are each formed by a cylindrical drum;
the first axis is a cylinder axis of the first sample holding part; and
the second axis is a cylinder axis of the second sample holding part.

3. The double motor rheometer according to claim 1, further comprising:
at least part of a first drive train by way of which the first sample holding part is connected or connectable, in terms of driving, to the first measuring motor; and
at least part of a second drive train by way of which the second sample holding part is connected or connectable, in terms of driving, to the second motor;
wherein at least one of the first drive train and of the second drive train is gearless.

4. The double motor rheometer according to claim 1, further comprising:
a control device for controlling the first measuring motor and the second measuring motor and thus effecting an extension of the sample between the first sample holding part and the second sample holding part.

5. The double motor rheometer according to claim 4, wherein the control device is configured for determining a torsional moment generated by the first measuring motor and/or a torsional moment generated by the second measuring motor.

6. The double motor rheometer according to claim 1, wherein
the first sample holding part and the second sample holding part are each formed by a cylindrical drum;
the first axis is a cylinder axis of the first sample holding part; and
the second axis is a cylinder axis of the second sample holding part.

7. The double motor rheometer according to claim 1, further comprising:
at least part of a first drive train by way of which the first sample holding part is connected or connectable, in terms of driving, to the first measuring motor; and
at least part of a second drive train by way of which the second sample holding part is connected or connectable, in terms of driving, to the second motor;
wherein at least one of the first drive train and of the second drive train is gearless.

8. The double motor rheometer according to claim 1, further comprising:
a control device for controlling the first measuring motor and the second measuring motor and thus effecting an extension of the sample between the first sample holding part and the second sample holding part.

9. The double motor rheometer according to claim 1, further comprising:
a control device, wherein the control device is configured for determining a torsional moment generated by the first measuring motor and/or a torsional motor generated by the second measuring motor.

10. The double motor rheometer according to claim 1, further comprising:
a control device, wherein the control device is configured for controlling the first measuring motor and the second measuring motor in order to impose an extension profile that oscillates over time to the sample between the first sample holding part and the second sample holding part.

11. The double motor rheometer according to claim 1, further comprising:
a control device, wherein the control device is configured for controlling the first measuring motor and the second measuring motor in order to impose a combined extension profile comprising extension and oscillation to the sample between the first sample holding part and the second sample holding part.

12. A method for controlling a double motor rheometer, the method comprising:
providing a rheometer base, the rheometer base including a first measuring motor and a second measuring motor;
providing, attached to the first measuring motor, a first sample holding part that when driven by the first measuring motor rotates about a first axis and, attached to a second measuring motor, a second sample holding part that when driven by the second measuring motor rotates about a second axis parallel to and spaced apart from the first axis;
displacing at least one of the first measuring motor and the second measuring motor from a first position to a different second position in a direction transverse to the first axis;
introducing a sample between the first sample holding part and the second sample holding part; and
controlling the first measuring motor and the second measuring motor to thereby effect an extension of the sample.

13. The method according to claim 12, further comprising:
controlling the first measuring motor and the second measuring motor in order to impose an extension profile that oscillates over time to the sample between the first sample holding part and the second sample holding part.

14. The method according to claim 12, further comprising:
controlling the first measuring motor and the second measuring motor in order to impose a combined extension profile comprising extension and oscillation to the sample between the first sample holding part and the second sample holding part.

15. The method according to claim 12, further comprising:
determining a first torsional moment generated by the first measuring motor;
determining a second torsional moment generated by the second measuring motor;
calculating an average value from the first torsional moment and the second torsional moment; and
controlling at least one of the first measuring motor and the second measuring motor in response to the average value.

16. A computer program product for controlling a rheometer, which computer program product, when executed on a processor device, is configured to implement the method according to claim 12.

* * * * *